(12) United States Patent
Raft et al.

(10) Patent No.: US 12,075,218 B2
(45) Date of Patent: Aug. 27, 2024

(54) HEARING PROTECTION APPARATUS AND SYSTEM WITH SOUND SOURCE LOCALIZATION, AND RELATED METHODS

(71) Applicant: Falcom A/S, Ballerup (DK)

(72) Inventors: Casper Silbo Raft, Ballerup (DK); Søren Christian V. Pedersen, Valby (DK); Jesse Caster, Ontario, NY (US)

(73) Assignee: Falcom A/S, Ballerup (DK)

( * ) Notice: Subject to any disclaimer, the term of this patent is extended or adjusted under 35 U.S.C. 154(b) by 122 days.

(21) Appl. No.: 17/843,958

(22) Filed: Jun. 18, 2022

(65) Prior Publication Data
US 2022/0322001 A1  Oct. 6, 2022

Related U.S. Application Data

(63) Continuation of application No. PCT/EP2020/087130, filed on Dec. 18, 2020.

(30) Foreign Application Priority Data

Dec. 20, 2019  (EP) ..................................... 19218931

(51) Int. Cl.
  *H04R 3/00*  (2006.01)
  *G01S 3/808*  (2006.01)
  *H04R 1/40*  (2006.01)
(52) U.S. Cl.
  CPC ............ *H04R 3/005* (2013.01); *G01S 3/8083* (2013.01); *H04R 1/406* (2013.01); *H04R 2410/01* (2013.01); *H04R 2460/01* (2013.01)
(58) Field of Classification Search
  CPC .... H04R 3/005; H04R 1/406; H04R 2410/01; H04R 2460/01; G01S 3/8083
  (Continued)

(56) References Cited

U.S. PATENT DOCUMENTS

| 2005/0117771 A1 | 6/2005 | Vosburgh et al. |
| 2012/0212399 A1 | 8/2012 | Border et al. |

(Continued)

FOREIGN PATENT DOCUMENTS

| EP | 2866464 | 4/2015 |
| WO | WO 2017/223469 | 12/2017 |

OTHER PUBLICATIONS

PCT International Search Report and Written Opinion for International Appln. No. PCT/EP2020/087130 dated Mar. 16, 2021.

(Continued)

*Primary Examiner* — Vivian C Chin
*Assistant Examiner* — Douglas J Suthers
(74) *Attorney, Agent, or Firm* — Vista IP Law Group, LLP

(57) ABSTRACT

A hearing protection apparatus, a related method, and a server device is disclosed. The hearing protection apparatus comprises a set of microphones comprising a first microphone and a second microphone; a first positioning device for provision of first position data of the hearing protection apparatus; and a communication device connectable to the first microphone and the second microphone and the first positioning device, the communication device comprising a processing unit and an interface; wherein the processing unit is configured to: obtain a first audio input signal from the first microphone and a second audio input signal from the second microphone; determine first audio data based on the first audio input signal and the second audio input signal; and transmit the first audio data and the first position data to a radio unit.

19 Claims, 4 Drawing Sheets

(58) Field of Classification Search
USPC .......................................... 381/71.6, 26, 92
See application file for complete search history.

(56) References Cited

U.S. PATENT DOCUMENTS

| | | |
|---|---|---|
| 2016/0125885 A1 | 5/2016 | Betts et al. |
| 2017/0374455 A1* | 12/2017 | Shastry .................. H04R 3/005 |
| 2018/0139566 A1 | 5/2018 | Crum |
| 2019/0318719 A1 | 10/2019 | Copt et al. |

OTHER PUBLICATIONS

PCT International Search Report and Written Opinion for International Appln. No. PCT/EP2020/087136 dated Mar. 10, 2021.
PCT International Search Report and Written Opinion for International Appln. No. PCT/EP2020/087147 dated Jan. 21, 2021.

\* cited by examiner

HEARING PROTECTION APPARATUS AND SYSTEM WITH SOUND SOURCE LOCALIZATION, AND RELATED METHODS

RELATED APPLICATION DATA

This application is a continuation of International Patent Application No. PCT/EP2020/087130 filed on Dec. 18, 2020, which claim priority to and the benefit of European Patent Application No. 19218931.4 filed on Dec. 20, 2019. The entire disclosures of the above applications are expressly incorporated by reference herein.

FIELD

The present disclosure relates to a hearing protection apparatus and related methods including a method of operating a hearing protection apparatus.

BACKGROUND

In combat situations or other stressed environments with a high noise level, it is desirable for a user to effectively protect his/her hearing while enabling the user to communicate with teammates via radio or other communication systems. During combat situations or other stressed environments, a user may need to wear a hearing protection device to attenuate noise, e.g. from gunfire, machinery and other types of constant or intermittent noise.

A drawback of using radio communication is that directional cues may be lost, causing the user to struggle in locating the source of an input signal, which may be dangerous in particular in combat situations, where the risk of friendly fire is heavily increased when directional cues are lost.

SUMMARY

Accordingly, there is a need for hearing protection apparatuses and methods which increases the situational awareness of a user during combat situations or other stressed environments.

A hearing protection apparatus is disclosed comprising a set of microphones comprising a first microphone and a second microphone. The hearing protection apparatus comprises a first positioning device for provision of first position data of the hearing protection apparatus and a communication device connectable to the first microphone and the second microphone and the first positioning device. The communication device comprises a processing unit and an interface. The processing unit is configured to obtain a first audio input signal from the first microphone and a second audio input signal from the second microphone. The processing unit is further configured to determine first audio data based on the first audio input signal and second audio input signal. The processing unit is further configured to transmit the first audio data and the first position data to a radio unit.

Further, a method of operating a hearing protection apparatus comprising a set of microphones comprising a first microphone and a second microphone, and a first positioning device is provided. The method comprises obtaining a first audio input signal from a first microphone and a second audio input signal from a second microphone. The method comprises obtaining first position data from a first positioning device. The method comprises determining first audio data based on the first audio input signal and the second audio input signal. The method comprises transmitting the first audio data and the first position data to a radio unit.

Also disclosed is a server device for audio source monitoring in a communication system comprising a first communication device and the server device. The first communication device may be a communication device as disclosed herein. The server device comprises one or more processing units, a memory, and an interface. The server device is configured to obtain first audio data and first position data from the first communication device. The server is configured to determine a presence of an audio source event based on the first audio data and the first position data. The server is configured to output event data indicative of the audio source event.

It is an advantage of the present disclosure that the situational awareness of a user of the hearing protection device is enhanced in substantially real-time, which in turn reduces decision time.

Thus, a user of the communication device, e.g. in a combat situation, experiences improved situational awareness and localization of events, e.g. audio source events such as gunshots, explosions, or vehicles, and allies/teammates, or other events types e.g. approaching a dangerous area such as an enemy territory or a minefield, and/or position of enemies, which is highly beneficial for the mission-performing user/warfighter operating in enemy territories/combat situations.

Further, the user, such as mission-performing user/warfighter is provided with more precise and accurate localization/directional cues, so the mission-performing user/warfighter can accurately identify audio source events and teammates in the surrounding area while staying protected with hearing protection device and connected as well.

Further, directionality of input signal(s), such as audio input signal(s) from different sources can be improved, e.g. in turn providing a more effective spatial separation of sources in multi-source hearing protection apparatuses.

BRIEF DESCRIPTION OF THE DRAWINGS

The above and other features and advantages will become readily apparent to those skilled in the art by the following detailed description of exemplary hearing protection apparatuses, methods, and/or servers thereof with reference to the attached drawings, in which.

DETAILED DESCRIPTION

Figure 1:
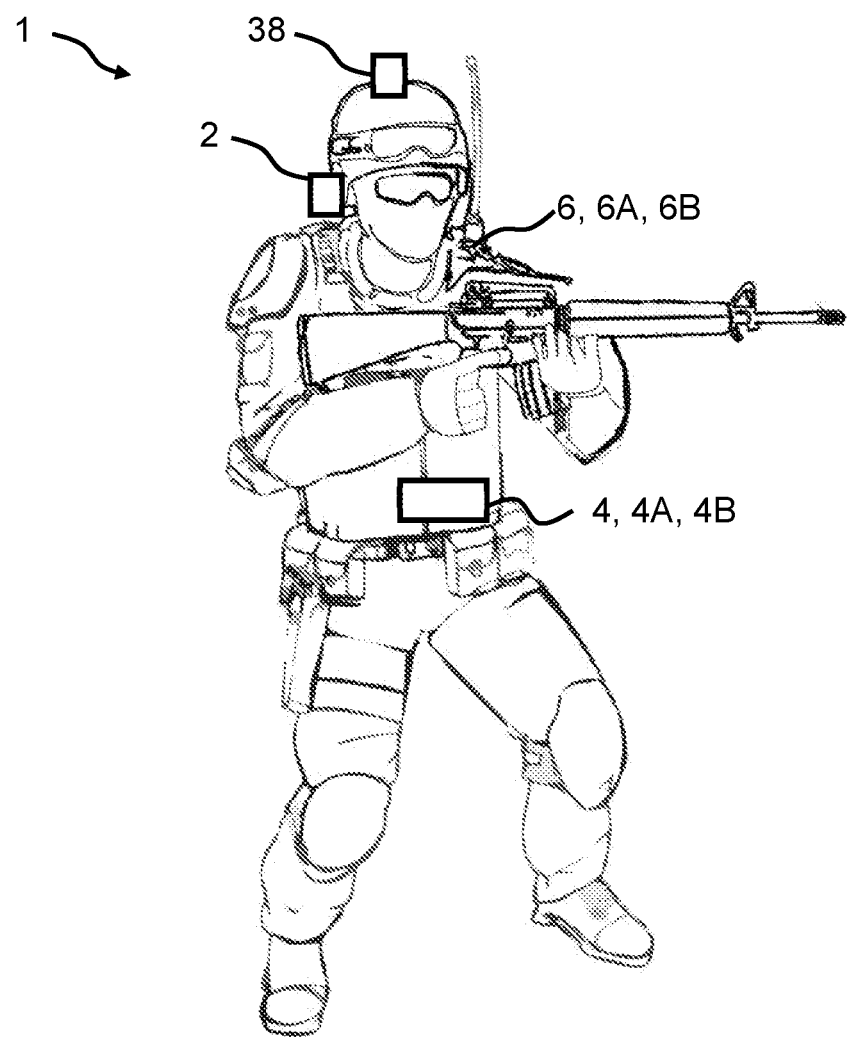
FIG. 1 schematically illustrates a mission-performing user wearing an exemplary hearing protection system comprising a hearing protection apparatus according to the disclosure.

Various exemplary hearing protection apparatuses, methods, and/or servers and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the hearing protection apparatuses, methods, and/or servers. They are not intended as an exhaustive description of the invention or as a limitation on the scope of the invention. In addition, the hearing protection apparatuses, methods, and/or server need not have all the aspects or advantages shown. An aspect or an advantage described in conjunction with a particular hearing protection apparatuses, methods, and/or server is not necessarily limited to that hearing protection apparatuses, methods, and/or server and can be practiced in any other hearing protection apparatuses, methods, and/or servers even if not so illustrated, or if not so explicitly described.

A hearing protection apparatus is disclosed. The hearing protection apparatus comprises a set of microphones comprising a first microphone and a second microphone.

The set of microphones may be positioned at different positions, for example when the hearing protection apparatus is worn by a user, the first microphone may be said to be positioned in a first position e.g. on one ear-side of the head of the user (such as a left ear-side of the user), and the second microphone being positioned in a second position e.g. on the other ear-side of the head the user (such as a right ear-side of the user). The hearing protection apparatus and the set of microphones may in one or more exemplary hearing protection apparatuses, methods, and/or servers comprise further microphones, such as a third microphone e.g. positioned at the top of the head of a user (such as on top of a head protection, such as a helmet). The third microphone may alternatively be positioned on the back on the user and/or the torso of the user. The third microphone may improve the determining of the direction of an audio source event, and thereby improve the source localization. By having the third microphone the hearing protection apparatus may improve the determining of whether the audio source event occurred behind the user or in front of the user. The hearing protection apparatus comprises a set of microphones.

The set of microphones may comprise one or more microphones. The set of microphones comprises a first microphone for provision of a first microphone input signal and/or a second microphone for provision of a second microphone input signal. The set of microphones may comprise N microphones for provision of N microphone signals, wherein N is an integer in the range from 1 to 10. In one or more exemplary hearing protection apparatus, the number N of microphones is two, three, four, five or more. The set of microphones may comprise a third microphone for provision of a third microphone input signal.

By having different positions on the head of the user, the set of microphones may be used to determine first audio data based on the first audio input signal and the second audio input signal.

The hearing protection apparatus comprises a first positioning device for provision of first position data of the hearing protection apparatus. The first positioning device may comprise a GPS device or unit, e.g. to provide first position data such as a first position of the user i.e. a first position of the hearing protection apparatus. The first position data may comprise a location coordinate or a position coordinate of the hearing protection apparatus. The first position data may include a first position and/or a first orientation/direction of the hearing protection apparatus/device i.e. a first orientation/direction of the head of the user wearing the hearing protection device. The first position data may thereby be indicative of a direction of the head of the user at the time where the first audio input signal and/or the second audio input signal are obtained. The first position data may thereby be used as a reference direction with regards to a direction of an audio source event. The first audio input signal and/or the second audio input signal may be linked to or correspond to a first orientation/direction, such that when the first audio data and the first position data are obtained and/or transmitted (e.g. streamed to the server device), a server device may be able to obtain and/or determine the direction of the audio source event with respect to the first orientation/direction of the head of the user. For example, a first direction of the head of the user may be linked to a first audio input signal and a second audio input signal, e.g. a set of a first audio input signal and a second audio input signal are obtained at times t1 and t2, and the first position data is received at a time t3, where t1 may be equal to t2, and t1<t3<t2 or t2<t3<t1. If the user does not change head direction, then one or more first audio input signals and/or second audio input signals may be linked to or correspond to the same first direction of the head of the user. The first audio data and the first position data may be transmitted such that a server device is able will be able to distinguish or use first audio input signals, second audio signals, and/or the first position data from a plurality of users.

A first direction of the audio source event may for example be determined (such as estimated or calculated) with head-related transfer function, HRTF, derivations e.g. using a first audio input signal from the first microphone and a second audio input signal from the second microphone and/or the first position data to determine the first direction of the audio source event. The first direction of the audio source event may be relative, e.g. to a first angular position, reference angular position, a variating angular position depending on the head direction of the user, and/or an absolute angular position. An advantage of providing first position data at the hearing protection apparatus is that the position data (position and/or direction) of the hearing protection apparatus may be obtained instantaneously. Further, by having the first position data at the hearing protection apparatus, the sending of position data to the server device may be reduced, e.g. by performing the processing of positioning data at the hearing protection apparatus.

The hearing protection apparatus comprises a communication device connectable to the first microphone, the second microphone, and the first positioning device.

The communication device comprises a processing unit and an interface. The communication device may comprise a memory, e.g. for storing the first audio data and/or the first position data. The interface may comprise a hearing protection device interface, such as one or more hearing protection device interfaces. The hearing protection device interfaces may allow the connection of the communication device to one or more hearing protection devices of the hearing protection apparatus of a mission-performing user, e.g. such that a first audio input signal and/or a second audio input signal are obtained from the one or more hearing protection devices, such as first microphone input signal from the first microphone and/or second microphone input signal from the second microphone.

The interface may comprise a radio unit interface, such as one or more radio unit interfaces. The one or more radio unit interfaces may allow connection of the communication device to one or more radio units of a hearing protection system of the user, e.g. such that the first audio data and the first position data may be transmitted to the one or more radio units and optionally to server device via the one or more radio units.

The processing unit is configured to obtain a first audio input signal also denoted first microphone input signal from the first microphone and a second audio input signal also denoted second microphone input signal from the second microphone. The first audio input signal may be generated by the first microphone, and the second audio input signal may be generated by the second microphone.

The first audio input signal and the second audio input signal may be indicative of a first sound, such as of one or more of the sound from a vehicle, a weapon, or a teammate speaking. The first audio input signal and/or the second audio input signal may be indicative of one or more of a gunshot sound, artillery fire sound, a driving vehicle sound, or a team mission performing user speaking sound. The first audio input signal and the second audio input signal may be indicative of the first sound, where the first sound is received at the first microphone at a first time and the first sound is received at the second microphone at a second time. The first time and the second time may be different and may comprise different time stamps. The first audio input signal and the second audio input signal may be indicative of the first sound, where the first sound is received at the first microphone at a first level or frequency-dependent first levels, and the first sound is received at the second microphone at a second level or frequency-dependent second levels. The first level and the second level may be different. The first audio input signal and the second audio input signal may be indicative of the first sound, where the first sound is received at the first microphone with a first frequency spectrum and the first sound is received at the second microphone with a second frequency spectrum. The first frequency spectrum may be different from the second frequency spectrum.

The processing unit is further configured to determine first audio data based on the first audio input signal and/or the second audio input signal.

The first audio data may comprise one or more time delays between the first audio input signal and the second audio input signal corresponding to the same sound. The first audio data may comprise one or more level differences between the first audio input signal and the second audio input signal corresponding to the same sound. The same sound may be received at different times at the first microphone and the second microphone.

Accordingly, the processing unit may be configured to determine one or more time delays between the first audio input signal and the second audio input signal and include the one or more time delays in the first audio data.

The first audio data may comprise one or more first levels of the first audio input signal, such as frequency-dependent first levels, e.g. a first level for each of a plurality of frequency bands. A first level may be an amplitude or power of the first audio input signal, e.g. in a specific frequency band.

The first audio data may comprise one or more second levels of the second audio input signal, such as frequency-dependent second levels, e.g. a second level for each of a plurality of frequency bands. A second level may be an amplitude or power of the second audio input signal, e.g. in a specific frequency band.

The first audio data may comprise one or more third levels of a third audio input signal, such as frequency-dependent third levels, e.g. a third level for each of a plurality of frequency bands. A third level may be an amplitude or power of the third audio input signal, e.g. in a specific frequency band.

Accordingly, the processing unit may be configured to determine one or more first levels of the first audio input signal and/or one or more levels of the second audio input signal and optionally include the first level(s) and/or the second level(s) in the first audio data.

The processing unit may be configured to determine one or more third levels of a third audio input signal and optionally include the third level(s) in the first audio data.

The processing unit may be configured to determine one of more level differences, such as a plurality of frequency-dependent level differences, between a first level and a second level and optionally include the level difference(s) in the first audio data.

Accordingly, the first audio data may comprise one of more level differences, such as a plurality of frequency-dependent level differences, between a first level and a second level.

The first audio data may comprise one or more time stamps such as one or more first time stamps related or associated with the first audio input signal and/or one or more second time stamps related or associated with the second audio input signal.

By including only relevant audio parameters in the first audio data and not the complete audio input signal, the transmission bandwidth requirements are reduced and optimized.

The first audio data may comprise a direction of the first sound e.g. the direction from where the first sound comes from with respect to the direction of the head of the user, a distance to a sound or a position of interest, and/or a relative direction such as an angle indicating a range or radius of where a sound comes from or of where a position of interest is with respect to the hearing protection apparatus/device. The first audio data may for example be determined (such as estimated or calculated) with head-related transfer function, HRTF, derivations e.g. using the first audio input signal from the first microphone and the second audio input signal from the second microphone and/or the first position data. By using HRTF derivations combined with first position data, an improved accuracy of localization of a sound source may be achieved, and front-back errors (errors in determining whether an audio source event occurred in front of or behind the user) may be reduced or avoided. Accordingly, the processing unit may be configured to determine a direction of the first sound based on one or more, such as all of the first audio input signal, the second audio input signal, and optionally the third audio input signal.

In one or more exemplary hearing protection apparatuses, methods, and/or servers, the processing unit is further configured to determine first audio data based on the first audio input signal, the second audio input signal, and the first position data.

The processing unit is further configured to transmit the first audio data and/or the first position data to a radio unit, e.g. via the interface. The first audio data may be aligned in time with the position data. In one or more exemplary hearing protection apparatuses, the first position data comprises one or more position time stamps, the position time stamps being indicative of a time of the position data. In accordance with transmitting the first audio data and the first position data to the radio unit, the first audio data and the first position data may then be transmitted to a server device being configured to process the first audio data and the first position data e.g. to determine the presence of the audio source event at the server device. An advantage of determining the presence of the audio source event at the server device, may be that the processing required to perform the determining calculations may require big amounts processing power and may therefore be power consuming. It may therefore be an advantage to perform the determining at the server device instead of at the hearing protection apparatus. The determining of the presence of the audio source event may alternatively be performed partially at the hearing protection apparatus and partially at the server device. For example, the part of the determining requiring most processing power being performed at the server device to reduce the power usage of the processing unit at the hearing protection apparatus, and the rest being performed at the hearing protection apparatus to reduce the transmitting of data back and forth to the server device, which also may be power consuming.

In one or more exemplary hearing protection apparatuses, methods, and/or servers, the processing unit is configured to determine a presence of an audio source event based on the first audio input signal and the second audio input signal. In accordance with determining the presence of an audio source event, the processing unit may be configured to transmit, to the radio unit, first audio data such as event data indicative of the audio source event. The first audio data may be indicative of an audio source event. The first audio data may be associated with an audio source event. In other words, the first audio data may comprise event data indicative of an audio source event. First audio data, such as event data may include event type, event time, duration of event, and/or distance to audio source event from the hearing protection apparatus. To determine a presence of an audio source event may comprise to select an audio source event to be a source of interest for the user of the hearing protection apparatus. The selection of a source of interest may be based e.g. on the event data such as depending on event type, event time, duration of event, and/or distance to audio source event from the hearing protection apparatus. The audio source event may for example be indicative of a gunshot or gunfire, an explosion, a vehicle sound, and/or a teammate sound. For example, if audio input signal indicative of a gunshot sound that occurred close to the user is obtained, the gunshot may then be determined as an audio source event. The gunshot sound may then be categorised as a source of interest, e.g. based on one or more of a first direction of the gunshot, level of the gunshot, and/or position from where the gunshot was fired (e.g. friendly fire may for example be close whereas enemy fire may for example be further away).

In one or more exemplary hearing protection apparatuses, the processing unit is configured to determine audio source event data, such as one or more or audio source event type, audio source event time, duration of audio source event, direction of audio source event and distance to audio source event, based on the first audio input signal and the second audio input signal, and optionally include the event data in the first audio data.

In accordance with a determination that an audio source event is present, the processing unit may be configured to determine a first audio output signal based on first audio data indicative of the audio event and/or based on the first position data. The first audio output signal may be an informative audio output giving an indication e.g. of the type of audio source event of which the presence was determined. For example, the first audio output signal may be a sound alert indicating that an enemy fired a sniper shot. The first audio output signal may be a contextual audio output giving a contextual information indicative of the type of audio source event that occurred and from which direction relative to the user the audio source event occurred.

To determine a first audio output signal may comprise to generate a first audio output at the hearing protection apparatus and/or at the server device. To determine a first audio output signal may comprise to combine a first audio output signal generated at the hearing protection apparatus and a first audio output signal generated at the server device. The first audio output signal may be determined based on one or more or a combination of sound samples, sound pieces, or sound files stored on the memory of the communication device, sound samples, sound pieces, or sound files stored on the memory of the server device, and/or sound samples, sound pieces, or sound files generated based on the first audio input signal and the second audio input signal, at the hearing protection apparatus (e.g. the sound of a gunshot that is reproduced and outputted). The first audio output signal may comprise predetermined sound samples indicative of a given audio source event and/or first audio source event data based e.g. on a first audio output identifier, such as a given sound for a truck, a minefield, and/or an enemy. The first audio output signal may further comprise the combination of sound samples, such as combining a predetermined sound sample (such as a sound sample for indicating a truck), with a determined sound sample based on the position of the audio source event (indicative of a direction of the audio source event). For example, such a first audio output signal may comprise an alert saying, "vehicle from the right", which may be outputted e.g. through a right receiver and/or a left receiver of the hearing protection device of the user depending on the direction in which the user is looking i.e. the orientation of the hearing protection device. For example, if an audio source event has a direction to the right of the user at the time where it occurred, and that the user turned his/her head to the right afterwards, the first audio output signal may be outputted such that the user receives the indication that the audio source event is straight forward. The audio output signal may thereby "follow" the head direction of the use, if the head direction is changed.

In accordance with a determination that an audio source event is present, the processing unit is optionally configured to determine a second audio output signal based on first audio data indicative of the audio event and/or based on the first position data. The second audio output signal may be an informative audio output giving an indication e.g. of the type of audio source event of which the presence was determined. For example, the second audio output signal may be a sound alert indicating that an enemy fired a sniper shot. The second audio output signal may be a contextual audio output giving a contextual information indicative of the type of audio source event that occurred and from which direction relative to the head direction/orientation of the user the audio source event occurred. The processing unit may be configured to output the first audio output signal and the second audio output signal via the interface.

To output the first audio output signal via the interface may comprise to output a given first audio output signal (e.g. a given sound) from the memory, indicative of or corresponding to a given audio source event and/or given first audio source event data, based on the first audio output identifier. The first audio output signal may for example comprise a sound alert (for example if the user approaches a minefield or a gunshot position occurred in proximity of the user) or a guidance sound (for example to guide the user in direction of or away from a given event). The first audio output signal may vary in amplitude, pitch, etc, e.g. depending on the distance from the event or the type of audio source event. For example, if the user is close to a gunshot, the first audio output signal may have a higher amplitude such that the user is made aware that the danger may be close, while still being hearing protected from the gunshot sound. The first audio output signal may inform the user of the type of event by having a first audio output identifier, e.g. by having pre-stored voice commands, alerts, or messages indicative of or corresponding to a given event and/or given first event data, that may be outputted to the user. The first audio output signal may give a directional cue or information of where the audio source event and/or the first audio source event data comes from e.g. with respect to the head direction/orientation of the user, for example by outputting the first audio output signal via the interface to a first receiver of the hearing protection device and/or to a second receiver of the hearing protection device.

To output the first audio output signal via the interface may comprise to output the first audio output signal to the hearing protection device, e.g. to a first receiver of the hearing protection device and/or to a second receiver of the hearing protection device.

The first receiver may be a left receiver and the second receiver may be a right receiver, such that the first audio output signal may be outputted to the right and/or the left receiver, e.g. at different amplitudes, depending on the direction of the audio source event and/or the first audio source event data.

The event type may be determined based on a sound spectrum of the first audio input signal and/or the second audio input signal. For example, a vehicle sound may be mainly low frequency, whereas a gunshot sound may be of a broad spectrum.

In one or more exemplary hearing protection apparatuses, methods, and/or servers, it may be already known that the obtained sound is an audio source event e.g. a sound of interest. The audio source event may thereby be monitored by comparing the obtained first audio input signal and/or second audio input signal with the previously obtained first audio input signal and/or second audio input signal, for example to monitor if the user is approaching the audio source event, or if a driving vehicle is approaching the user. The comparing of the first audio input signals and/or second audio input signals may be based on one or more of a first primary parameter, a first secondary parameter, a second primary parameter, a second secondary parameter (such as changes in level and/or changes in time).

In one or more exemplary hearing protection apparatuses, methods, and/or servers, the first audio data comprises first direction data indicative of a first direction of the audio source event. In other words, the first audio data may comprise the first direction data.

In one or more exemplary hearing protection apparatuses, methods, and/or servers, the first audio data comprises a first primary parameter indicative of a level or levels of the first audio input signal. In other words, the first primary parameter may comprise physical characteristics indicative of level(s) of the first audio input signal, such as power or amplitude of the first audio input signal.

In one or more exemplary hearing protection apparatuses, methods, and/or servers, the first audio data comprises a first secondary parameter indicative of a timing of the first audio input signal. In other words, the first secondary parameter may comprise time characteristics indicative of a timing of the first audio input signal, such as a second time stamp.

In one or more exemplary hearing protection apparatuses, methods, and/or servers, the first audio data comprises a second primary parameter indicative of a level or levels of the second audio input signal. In other words, the second primary parameter may comprise physical characteristics indicative of a level of the second audio input signal, such as power or amplitude of the second audio input signal.

In one or more exemplary hearing protection apparatuses, methods, and/or servers, the first audio data comprises a second secondary parameter indicative of a timing of the second audio input signal. In other words, the second secondary parameter may comprise time characteristics indicative of a timing of the second audio input signal, such as a second time stamp.

The first audio input signal and the second audio input signal may be indicative of the first sound, where the first sound is received at the first microphone at first level(s) and the first sound is received at the second microphone at a second level(s). The first primary parameter may be indicative of the first level(s) and the second primary parameter may be indicative of the second level(s), where the first primary parameter and the second primary, such as the first level and the second level, may be different and may comprise one or more of different levels, such as powers and/or amplitudes.

The first audio input signal and the second audio input signal may be indicative of the first sound, where the first sound is received at the first microphone at a first time and the first sound is received at the second microphone at a second time. The first primary parameter may be indicative of the first time and the second primary parameter may be indicative of the second time, where the first primary parameter and the second primary, such as the first time and the second time, may be different and may comprise one or more of different durations and/or time stamps.

The first audio data may comprise one or more of a first amplitude, a first frequency range, and a first time interval indicative of a duration of the first audio input signal and/or one or more of a second amplitude, a second frequency range, and a second time interval indicative of a duration of the second audio input signal corresponding to a sound. Further, the first audio data may comprise audio type, audio time, duration of audio, and/or distance to audio source from the hearing protection apparatus.

In one or more exemplary hearing protection apparatuses, methods, and/or servers, the first positioning device comprises an accelerometer and/or a gyroscope.

The accelerometer and/or the gyroscope may e.g. provide first position data such as first direction or an angular orientation of the hearing protection device. The first positioning device may thereby provide a head direction of the user which may be used to determine a first direction of the audio source event. Thus, the first position data may comprise a first direction, such as a first head direction of the user (i.e. a first direction of the hearing protection device).

In one or more exemplary hearing protection apparatuses, methods, and/or servers, the first position data comprises a first position, such as GPS-coordinates. In other words, the first positioning device may comprise a GPS or other satellite-based position device.

In one or more exemplary hearing protection apparatuses, methods, and/or servers, the first audio data comprises a time delay or time delay parameter. In other words, the first audio data may comprise a time delay parameter indicative of a time delay between the first audio input signal and the second audio input signal.

The first audio input signal and the second audio input signal may be indicative of the first sound, where the first sound is received at the first microphone at a first time and the first sound is received at the second microphone at a second time. The first time and the second time may be different and may comprise different time stamps. The time delay parameter may be obtained based on or comprise the first time and/or the second time.

The presence of the audio source event may be determined based on the first audio data, e.g. based on the time delay parameter, and may for example be determined (such as estimated or calculated) with head-related transfer function, HRTF, derivations e.g. using the time delay parameter.

In one or more exemplary hearing protection apparatuses, methods, and/or servers, the first position data or the first audio data comprises first angular position data e.g. such as an angle indicating a range or radius of where a sound comes from or of where a sound of interest is.

The first angular position data may comprise a first angle indicative of the position of the audio source event relative to the user.

In one or more exemplary hearing protection apparatuses, methods, and/or server devices, to determine the presence of an audio source event comprises to determine an angle between a head direction of the user and a first direction of the audio source event.

The processing unit may be configured to obtain, e.g. via the interface and/or the first positioning device of the hearing protection apparatus, a user position signal indicative of a position of the user.

The processing unit is optionally configured to obtain, e.g. via the interface and/or the first positioning device, a first direction or a direction signal indicative of a head direction of the user. The first positioning device may comprise a first accelerometer and a second accelerometer.

The processing unit is optionally configured to determine a first angle, between the head direction and a first direction of the audio source event, from the user to the audio source event.

A method for operating a hearing protection apparatus comprising a set of microphones comprising a first microphone and a second microphone, and a first positioning device is disclosed.

The method comprises obtaining a first audio input signal from a first microphone and a second audio input signal from a second microphone. The method comprises obtaining first position data from a first positioning device.

The method comprises determining first audio data based on the first audio input signal and the second audio input signal.

The method comprises transmitting the first audio data and the first position data to a radio unit.

Further, a server device for audio source monitoring in a communication system comprising a first communication device and the server device is disclosed.

The server device comprises one or more processing units; memory; and an interface.

The server device is configured to obtain first audio data and first position data from the first communication device. The server device is configured to determine a presence of an audio source event based on the first audio data and/or the first position data. The server device is configured to output event data indicative of the audio source event.

In one or more exemplary server devices, the communication system comprises a second communication device. The server device is optionally configured to obtain second audio data and second position data from a second communication device of the communication system. The server device is optionally configured to determine a presence of an audio source event based on the first audio data, the first position data, the second audio data, and the second position data. The server device is configured to output event data indicative of the audio source event.

The server device is optionally configured to determine a presence of a first audio source event based on the first audio data and the first position data, and to determine a presence of a second audio source event based on the second audio data and the second position data. To output event data indicative of the audio source event may comprise transmitting first event data indicative of the first audio source event to the first communication device and/or to the second communication device. To output event data indicative of the audio source event may comprise transmitting second event data indicative of the second audio source event to the first communication device and/or to the second communication device.

It is to be understood that a description of a feature in relation to hearing protection apparatus(es) is also applicable to the corresponding method(s) and server device(s) and vice versa.

FIG. 1 shows an exemplary mission-performing user 1 wearing an exemplary hearing protection system comprising a radio unit 6 and a hearing protection apparatus according to some embodiments comprising a communication device and a hearing protection device 2. The hearing protection apparatus comprises a first positioning device 38. The first positioning device 38 is worn by the user on his helmet. The communication device 4 is here positioned on the torso of the user. The communication device may alternatively be worn on other body-parts of the user, such as the back, the arm, the leg, and/or the head (e.g. the helmet).

Figure 2:
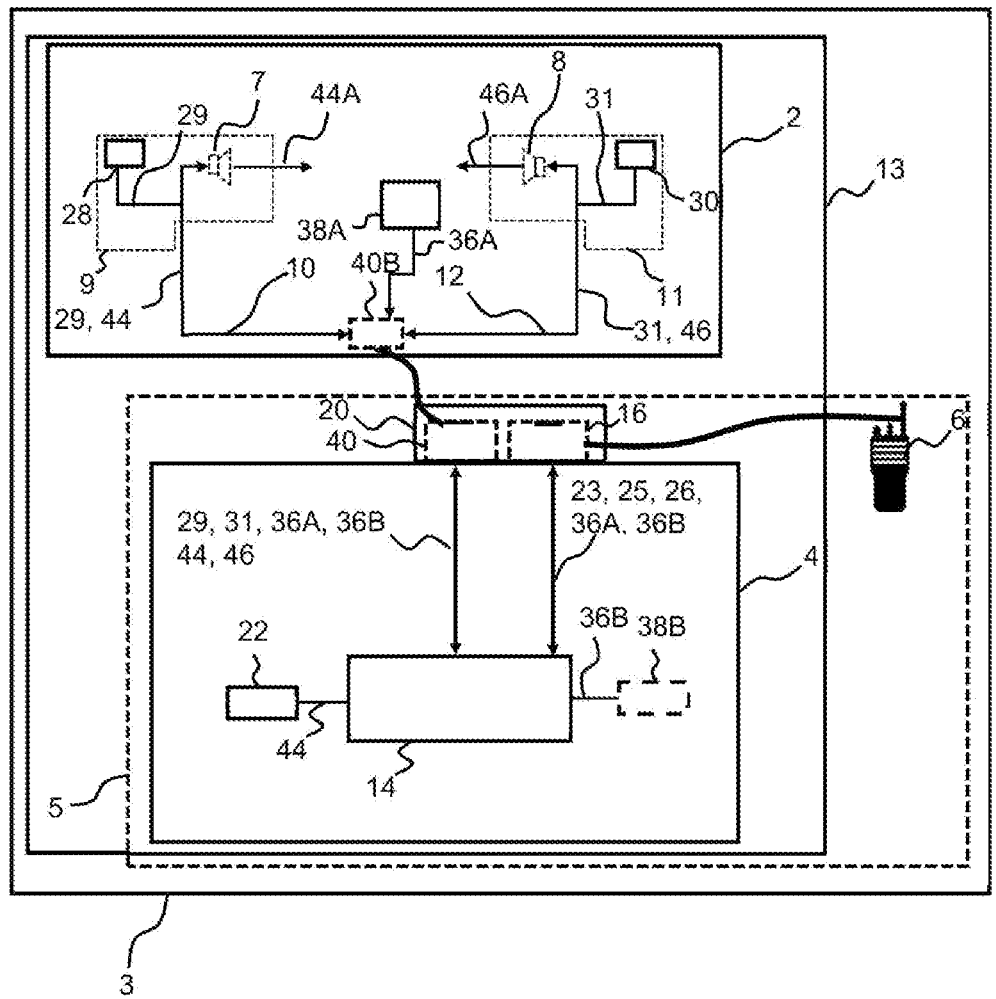
FIG. 2 is a block diagram of an exemplary hearing protection apparatus according to the disclosure.

FIG. 2 shows an exemplary hearing protection system 3 comprising a hearing protection apparatus 13 according to the disclosure and a radio unit 6. The hearing protection apparatus 13 comprises a set of microphones comprising a first microphone 28 and a second microphone 30. The hearing protection apparatus 13 comprises a first positioning device 38A for provision of first position data 36A, optionally including a first direction of the first positioning device (and hearing protection device/helmet/headgear on which the first positioning device is mounted) of the hearing protection apparatus 13. The hearing protection apparatus 13 comprises a communication device 4 connectable to the first microphone 28 and the second microphone 30 and the first positioning device 38A. The communication device 4 comprises a processing unit 14 and an interface 20. The processing unit 14 is configured to obtain a first audio input signal 29 from the first microphone 28 and a second audio input signal 31 from the second microphone 30. The processing unit 14 is further configured to determine first audio data based on the first audio input signal 29 and second audio input signal 31. The processing unit 14 is further configured to transmit the first audio data 25 and the first position data 36A to a radio unit 6, e.g. via the interface 20.

The communication device 4 comprises a processing unit 14, a memory 22, and an interface 20 connected to the processing unit 14. In one or more exemplary hearing protection apparatuses, the communication device 4 and the radio unit 6 may be comprised in a communication system 5. In one or more exemplary communication devices, the interface 20 comprises a hearing protection device interface 40 and/or a radio unit interface 16.

The hearing protection device interface 40 may allow the connection of the communication device 4 to the hearing protection device 2 of the hearing protection apparatus 13 of a mission-performing user 1, e.g. such that the first audio input signal 29 and the second audio input signal are obtained from the hearing protection device 2.

The radio unit interface 16 may allow the connection of the communication device 4 to the radio unit 6 of a hearing protection system 3 or a communication system 5 of the user, e.g. such that the first audio data 25 is transmitted via the radio unit 6.

In accordance with a determination that an audio source event is present, the processing unit 14 may be configured to determine a first audio output signal 44 based on first audio data 25 indicative of the audio event and/or based on the first position data 36A.

To output the first audio output signal 44 via the interface 20 may comprise to output the first audio output signal 44 to the hearing protection device 2, e.g. to a first receiver 7 of the hearing protection device 2. The first receiver 7 may be comprised in a first ear protector 9, such as a first earpiece or a first earmuff, of the hearing protection device 2, the first earpiece 9 comprising a first connection 10, such as a left connection.

The first receiver 7 may be a left receiver, such that the first audio output signal 44 may be outputted to the left receiver, e.g. at different amplitudes, depending on the direction of the event and/or the first event data and/or depending on the first direction of the head of the user. The first audio output signal 44 may be outputted by the first receiver 7 as a first audio output 44A.

The processing unit 14 may be configured to, e.g. in accordance with a determination that an audio source event is present, determine a second audio output signal 46 based on first audio data 25 indicative of the audio event and/or based on the first position data 36A.

To output the second audio output signal 46 via the interface 20 may comprise to output the second audio output signal 46 to the hearing protection device 2, e.g. to a second receiver 8 of the hearing protection device 2. The second receiver 8 may be comprised in a second ear protector 11, such as a second earpiece or a second earmuff, of the hearing protection device 2, the second earpiece 11 comprising a second connection 12, such as a right connection.

The second receiver 8 may be a right receiver, such that the second audio output signal 46 may be outputted to the right receiver, e.g. at different amplitudes, depending on the direction of the event and/or the first event data and/or depending on the first direction of the head of the user. The second audio output signal 46 may be outputted by the second receiver 8 as a second audio output 46A.

In one or more exemplary hearing protection apparatuses, the processing unit 14 is configured to determine a presence of an audio source event based on the first audio input signal 29 and the second audio input signal 31.

In one or more exemplary hearing protection apparatuses, the first audio data 25 comprises first direction data indicative of a first direction of the audio source event.

In one or more exemplary hearing protection apparatuses, the first audio data 25 comprises a first primary parameter indicative of a level of the first audio input signal 29, such as one or more first levels indicative of power or amplitude of the first audio input signal 29.

In one or more exemplary hearing protection apparatuses, the first audio data 25 comprises a first secondary parameter indicative of a timing of the first audio input signal 29.

In one or more exemplary hearing protection apparatuses, the first audio data 25 comprises a second primary parameter indicative of a level of the second audio input signal 31, such as one or more second levels indicative of power or amplitude of the second audio input signal 31.

In one or more exemplary hearing protection apparatuses, the first audio data 25 comprises a second secondary parameter indicative of a timing of the second audio input signal 31.

In one or more exemplary hearing protection apparatuses, the first positioning device 38A comprises an accelerometer and/or a gyroscope.

In one or more exemplary hearing protection apparatuses, the first position data 36A comprises a first position, such as GPS-coordinates.

In one or more exemplary hearing protection apparatuses, the first audio data 25 comprises a time delay parameter, e.g. indicative of a time delay between the first audio input signal and the second audio input signal.

In one or more exemplary hearing protection apparatuses, the first position data 25 or the first audio data comprises first angular position data e.g. such as an angle indicating a range and/or a radius of where a sound comes from or of where a sound of interest is.

In one or more exemplary hearing protection apparatuses, to determine the presence of an audio source event comprises to determine an angle between a head direction of the user and a first direction of the audio source event.

Figure 3:
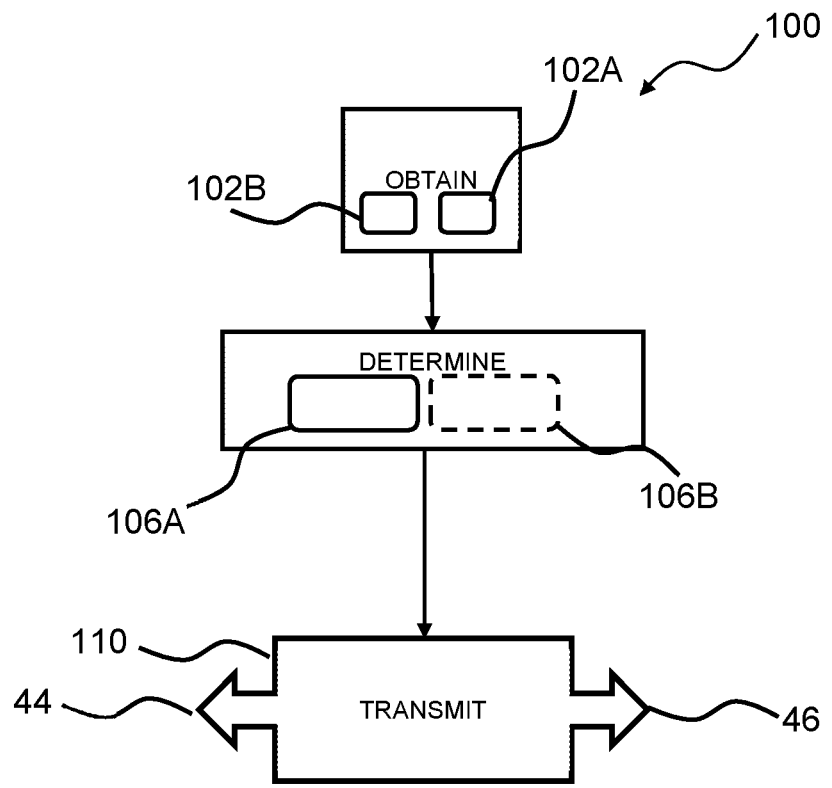
FIG. 3 is a flow diagram of an exemplary method according to the disclosure.

FIG. 3 is a flow diagram of an exemplary method of operating a hearing protection apparatus comprising a set of microphones comprising a first microphone and a second microphone, and a first positioning device.

The method 100 comprises obtaining 102A a first audio input signal from a first microphone and a second audio input signal from a second microphone.

The method 100 comprises obtaining 102B first position data from a first positioning device.

The method 100 comprises determining 106A first audio data based on the first audio input signal and the second audio input signal.

In one or more exemplary methods, the method comprises determining 106B a presence of an audio source event based on the first audio input signal and the second audio input signal.

The method 100 comprises transmitting 110 the first audio data and/or the first position data to a radio unit and/or a server device.

Figure 4:
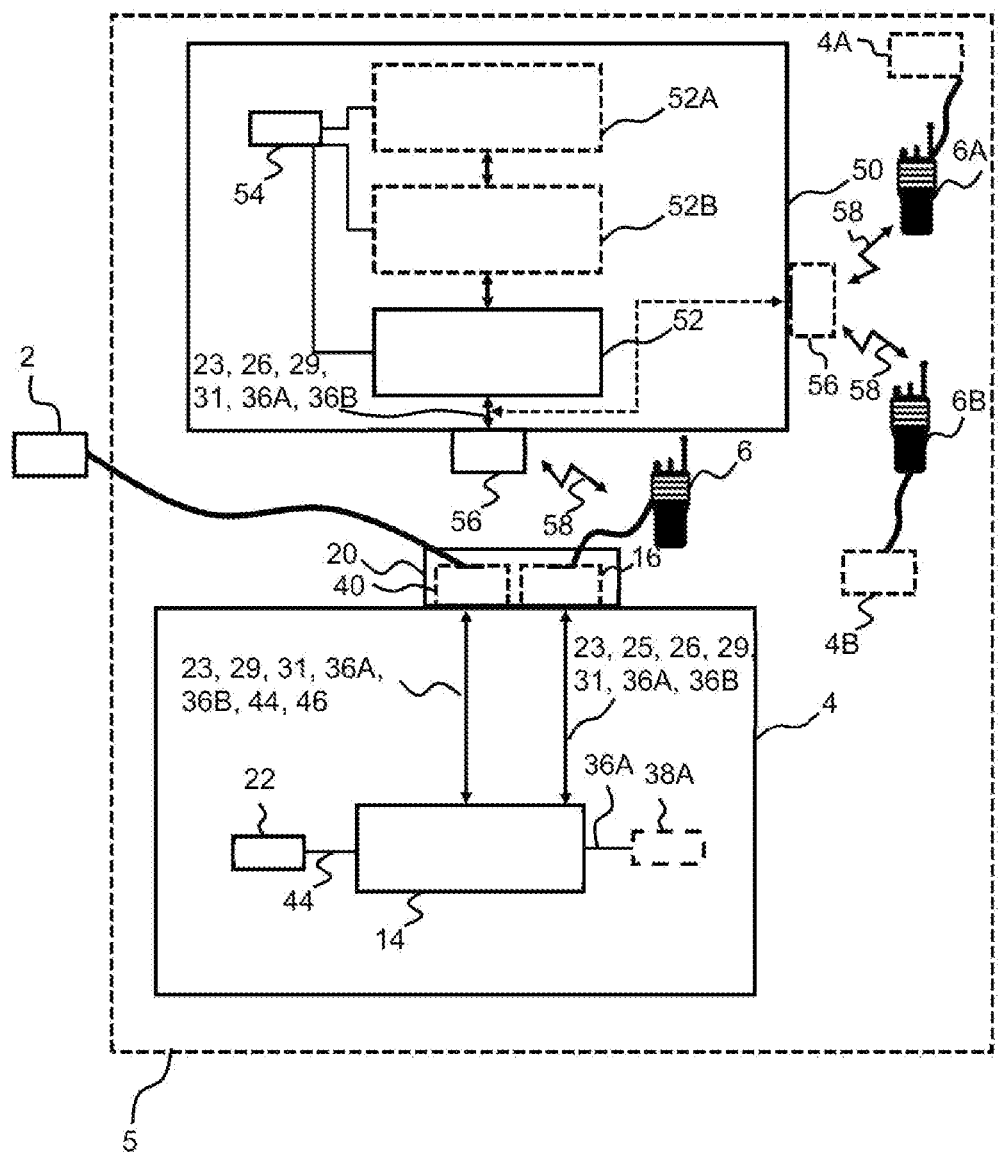
FIG. 4 is a block diagram of an exemplary server device according to the disclosure.

FIG. 4 shows an exemplary server device 50 for audio source monitoring in a communication system 5 comprising the server device 50 and a first communication device 4 for a hearing protection apparatus. The server device 50 comprises one or more processing units 52, 52A, 52B, a memory 54, and an interface 56. The server device 50 is configured to obtain first audio data 25 and first position data 36A from the communication device 4. The server device 50 is configured to determine a presence of an audio source event based on the first audio data and the first position data 36A. The server device 50 is configured to output event data 23 indicative of the audio source event e.g. via the interface 56.

In one or more exemplary server devices, the server device 50 is configured to output the event data 23 via the interface 56 to a radio unit 6, through a connection 58. The connection 58 may be wireless, such as a radio connection, or a wired connection.

In one or more exemplary server devices, the server device 50 is configured to output the event data 23 via the interface 56 to a radio unit 6A/communication device 4A, through a connection 58.

In one or more exemplary server devices, the communication system 5 comprises a second communication device 4B. In one or more exemplary server devices, the server device 50 is configured to output the event data 23 via the interface 56 to a radio unit 6B/communication device 4B, through a connection 58.

The server device 50 is optionally further configured to obtain second audio data 26 and second position data 36B from a second communication device 4A of the communication system 5. The server device 50 is configured to determine a presence of the audio source event based on the first audio data 25, the first position data 36A, the second audio data 26, and the second position data 36B. The server device is configured to output event data 23 indicative of the audio source event.

In one or more exemplary server devices, the server device 50 is configured to obtain position data 36A, 36B via the interface 56. The server device 50 is configured to determine a presence of an event based on the position data 36A and/or 36B.

In one or more exemplary server devices, the server device 50 is configured to output the event data 23 via the interface 56 to a second radio unit 6A configured to communicate with a second communication device 4A of a second hearing protection apparatus, and a third radio unit 6B configured to communicate with a third communication device 4B of a third hearing protection apparatus.

For example, in a multi-user system where a plurality of user-performing users having a plurality of hearing protection apparatuses communicating with the server device, the server device may be configured to obtain first audio data and first position data from the plurality of hearing protection apparatuses. To determine a presence of the audio source event may therefore be based on a plurality of audio data and position data from different hearing protection apparatuses.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-4 comprise some modules or operations which are illustrated with a solid line and some modules or operations which are illustrated with a dashed line. The modules or operations which are comprised in a solid line are modules or operations which are comprised in the broadest example hearing protection apparatuses, methods, and/or server. The modules or operations which are comprised in a dashed line are example hearing protection apparatuses, methods, and/or servers which may be comprised in, or a part of, or are further modules or operations which may be taken in addition to the modules or operations of the solid line example hearing protection apparatuses, methods, and/or servers. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary hearing protection apparatuses, methods, and/or servers may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 mission-performing user
2 hearing protection device
3 hearing protection system
4, 4A, 4B communication device
5 communication system
6, 6A, 6B radio unit
7 first receiver
8 second receiver
9 first ear protector, first earpiece, first earmuff
10 first connection
11 second ear protector, second earpiece, second earmuff
12 second connection
13 hearing protection apparatus
14 processing unit
16 radio unit interface
20 interface
22 memory
23 event data
25 first audio data
26 second audio data
28 first microphone
29 first audio input signal
30 second microphone
31 second audio input signal
36A first position data
36B second position data
38, 38A first positioning device
38B hearing protection device position module
40, 40B hearing protection device interface
42 sensor device
44 first audio output signal
44A first audio output 46 second audio output signal
46A second audio output
50 server device
52, 52A, 52B processing units
54 memory
56 interface
58 connection
100 method of operating a hearing protection apparatus
102A obtaining a first audio input signal from a first microphone and a second audio input signal from a second microphone
102B obtaining first position data from a first positioning device
106A determining first audio data based on the first audio input signal and the second audio input signal
106B determining a presence of an audio source event based on the first audio input signal and the second audio input signal
110 transmitting the first audio data and the first position data to a radio unit

The invention claimed is:

1. A hearing protection apparatus comprising:
a set of microphones comprising a first microphone and a second microphone;
a first positioning device for provision of first position data of the hearing protection apparatus; and
a communication device connectable to the first microphone and the second microphone and the first positioning device, the communication device comprising a processing unit and an interface;
wherein the processing unit of the communication device is configured to:
obtain a first audio input signal from the first microphone of the hearing protection apparatus, and a second audio input signal from the second microphone of the hearing protection apparatus;
determine first audio data based on the first audio input signal and the second audio input signal; and
transmit the first audio data and the first position data to a radio unit.

2. The hearing protection apparatus according to claim 1, wherein the processing unit is configured to determine a presence of an audio source event based on the first audio input signal and the second audio input signal.

3. The hearing protection apparatus according to claim 2, wherein the first audio data comprises directional information indicative of a first direction of the audio source event.

4. The hearing protection apparatus according to claim 1, wherein the first audio data comprises a parameter indicative of a level of the first audio input signal.

5. The hearing protection apparatus according to claim 1, wherein the first audio data comprises a parameter indicative of a timing of the first audio input signal.

6. The hearing protection apparatus according to claim 1, wherein the first audio data comprises a first parameter indicative of a level of the first audio input signal, and a second parameter indicative of a level of the second audio input signal.

7. The hearing protection apparatus according to claim 1, wherein the first audio data comprises a first parameter indicative of a timing of the first audio input signal, and a second parameter indicative of a timing of the second audio input signal.

8. The hearing protection apparatus according to claim 1, wherein the first positioning device comprises an accelerometer and/or a gyroscope.

9. The hearing protection apparatus according to claim 1, wherein the first audio data comprises a time delay parameter.

10. The hearing protection apparatus according to claim 1, wherein the first position data comprises first angular position data.

11. The hearing protection apparatus according to claim 1, wherein the set of microphones comprises a third microphone, and wherein the processing unit is configured to obtain a third audio input signal from the third microphone, and to determine first audio data based also on the third audio input signal.

12. The hearing protection apparatus according to claim 1, wherein the processing unit is configured to transmit the first audio data and the first position data to the radio unit in association with each other.

13. The hearing protection apparatus according to claim 1, wherein the first position data comprises a position time stamp, and wherein the processing unit is configured to provide the position time stamp to the radio unit.

14. The hearing protection apparatus according to claim 1, wherein the radio unit is configured to perform wireless transmission of the first audio data and the first position data in association with each other for the hearing protection apparatus.

15. A hearing protection apparatus comprising:
a set of microphones comprising a first microphone and a second microphone;
a first positioning device for provision of first position data of the hearing protection apparatus; and
a communication device connectable to the first microphone and the second microphone and the first positioning device, the communication device comprising a processing unit and an interface;
wherein the processing unit of the communication device is configured to:
obtain a first audio input signal from the first microphone of the hearing protection apparatus, and a second audio input signal from the second microphone of the hearing protection apparatus;
determine first audio data based on the first audio input signal and the second audio input signal; and
transmit the first audio data and the first position data to a radio unit;
wherein the first position data comprises a GPS-coordinate.

16. A method performed by a hearing protection apparatus comprising a first microphone, a second microphone, and a first positioning device, the method comprising:
obtaining a first audio input signal from the first microphone of the hearing protection apparatus;
obtaining a second audio input signal from the second microphone of the hearing protection apparatus;
obtaining first position data from the first positioning device of the hearing protection apparatus;
determining first audio data based on the first audio input signal and the second audio input signal; and
transmitting the first audio data and the first position data to a radio unit.

17. A server device for audio source monitoring in a communication system comprising a first communication device and the server device, the server device comprising:
one or more processing units;
a memory; and
an interface,
wherein the server device is configured to:

obtain first audio data and first position data from the first communication device;

determine a presence of an audio source event based on the first audio data and the first position data; and output event data indicative of the audio source event;

wherein the communication system comprises a second communication device, and wherein the server device is further configured to obtain second audio data and second position data from the second communication device of the communication system;

wherein the presence of the audio source event is determined also based on the second audio data and the second position data.

18. The server device according to claim 17, wherein the first position data is provisioned by a sensor at a hearing device.

19. The server device according to claim 17, wherein the first audio data is based on microphone output provisioned by a microphone at a hearing device.

* * * * *